United States Patent [19]

Jones et al.

[11] Patent Number: 4,554,395

[45] Date of Patent: Nov. 19, 1985

[54] METHANE CONVERSION

[75] Inventors: C. Andrew Jones, Newtown Square; John J. Leonard, Springfield; John A. Sofranko, West Chester, all of Pa.

[73] Assignee: Atlantic Richfield Company, Los Angeles, Calif.

[21] Appl. No.: 522,935

[22] Filed: Aug. 12, 1983

Related U.S. Application Data

[63] Continuation-in-part of Ser. No. 412,649, Aug. 30, 1982, abandoned.

[51] Int. Cl.$^4$ .............................................. C07C 2/00
[52] U.S. Cl. .................................. 585/500; 585/417; 585/418; 585/541; 585/654; 585/656; 585/658; 585/700; 585/943
[58] Field of Search ............... 585/500, 541, 700, 654, 585/658, 400, 417, 943, 656, 418

[56] References Cited

U.S. PATENT DOCUMENTS

| | | | |
|---|---|---|---|
| 1,995,136 | 3/1935 | Winkler et al. | 585/500 |
| 2,216,130 | 10/1940 | Pier et al. | 585/943 |
| 2,326,799 | 8/1943 | Pier et al. | 585/700 |
| 2,608,534 | 8/1952 | Fleck | 585/654 |
| 3,900,525 | 8/1975 | Christmann et al. | 585/541 |
| 4,066,704 | 1/1978 | Harris et al. | 585/658 |
| 4,205,194 | 5/1980 | Mitchell et al. | 585/500 |
| 4,239,658 | 12/1980 | Mitchell et al. | 585/500 |

FOREIGN PATENT DOCUMENTS 255829  5/1926  United Kingdom ............... 585/700

OTHER PUBLICATIONS

Keller, G. E., "Synthesis of Ethylene via Oxidative Coupling of Methane", J. of Catalysis, 73, 9–19 (1982).
Fang, T. and Yeh, C., "Catalytic Pyrolysis of Methane", J. Chinese Chem. Soc., 29, 265–273, 1981.

Primary Examiner—William R. Dixon, Jr.
Assistant Examiner—Cynthia A. Prezlock
Attorney, Agent, or Firm—Craig E. Larson

[57] ABSTRACT

A method for synthesizing hydrocarbons from a methane source which comprises contacting methane with an oxidative synthesizing agent under elevated pressures, preferably at pressures within the range of about 5 to 30 atmospheres. Particularly effective oxidative synthesizing agents are reducible oxides of metals selected from the group consisting of Mn,Sn,In,Ge,Pb,Sb, and Bi.

38 Claims, 1 Drawing Figure

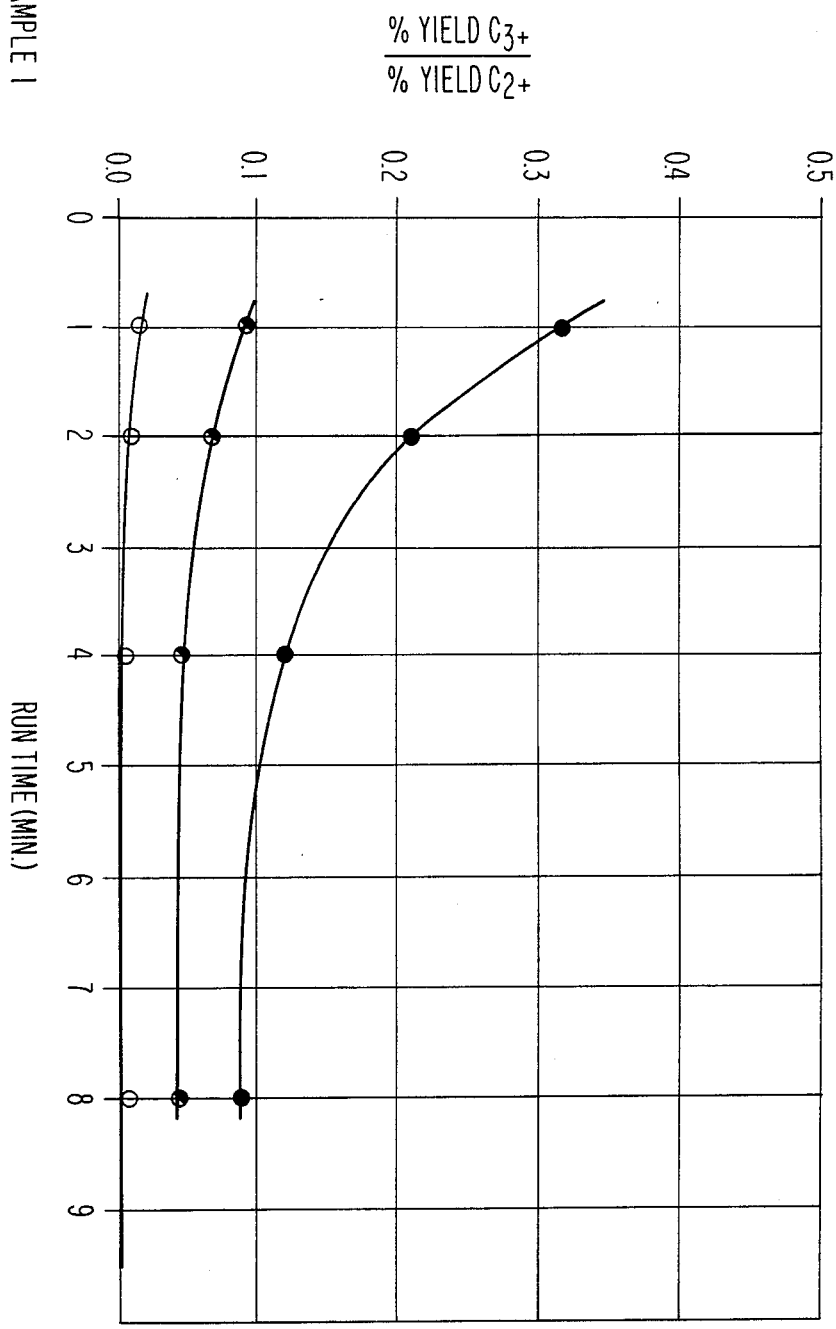

METHANE CONVERSION

CROSS REFERENCED TO RELATED CASES

This application is a continuation-in-part of U.S. application Ser. No. 412,649, filed Aug. 30, 1982, abandoned.

This application is related to copending, concurrently-filed U.S. patent application Ser. Nos. 522,925 now U.S. Pat. No. 4,443,649; 522,944 now U.S. Pat. No. 4,444,984; 522,942 now U.S. Pat. No. 4,443,648; 522,905 now U.S. Pat. No. 4,443,649; 522,877; 522,876; 522,906 now U.S. Pat. No. 4,443,646; and Ser. No. 522,938, the entire content of which are incorporated herein by reference.

BACKGROUND OF THE INVENTION

1. Field of the Invention

This invention relates to synthesis of hydrocarbons from a methane source. A particular application of this invention is a method for converting natural gas to more readily transportable material.

2. Description of the Prior Art

A major source of methane is natural gas. Other sources of methane have been considered for fuel supply, e.g., the methane present in coal deposits or formed during mining operations. Relatively small amounts of methane are also produced in various petroleum processes.

The composition of natural gas at the wellhead varies but the major hydrocarbon present is methane. For example the methane content of natural gas may vary within the range of from about 40 to 95 vol. %. Other constituents of natural gas may include ethane, propane, butanes, pentane (and heavier hydrocarbons), hydrogen sulfide, carbon dioxide, helium and nitrogen.

Natural gas is classified as dry or wet depending upon the amount of condensable hydrocarbons contained in it. Condensable hydrocarbons generally comprise $C_3+$ hydrocarbons although some ethane may be included. Gas conditioning is required to alter the composition of wellhead gas, processing facilities usually being located in or near the production fields. Conventional processing of wellhead natural gas yields processed natural gas containing at least a major amount of methane.

Large-scale use of natural gas often requires a sophisticated and extensive pipeline system. Liquefaction has also been employed as a transportation means, but processes for liquefying, transporting, and revaporizing natural gas are complex, energy-intensive, and require extensive safety precautions. Transport of natural gas has been a continuing problem in the exploitation of natural gas resources. It would be extremely valuable to be able to convert methane (e.g., natural gas) to more easily handleable, or transportable, products. Moreover, direct conversion to olefins such as ethylene or propylene would be extremely valuable to the chemical industry.

In addition to its use as fuel, methane is used for the production of halogenated products (e.g., methyl chloride, methylene chloride, chloroform and carbon tetrachloride). Methane has also been used as a feedstock for producing acetylene by electric-arc or partial-oxidation processes. Electric-arc processes are operated commercially in Europe. In partial-oxidation processes, a feed mixture of oxygen and methane (the methane may contain other, additional hydrocarbons) are preheated to about 540° C. and ignited in a burner. Representative processes of this type are disclosed in U.S. Pat. Nos. 2,679,544; 3,234,300; and 3,244,765. Partial oxidation produces significant quantities of CO, $CO_2$ and $H_2$, yielding a dilute acetylene-containing gas and thereby making acetylene recovery difficult.

The largest, non-fuel use of methane is in the production of ammonia and methanol (and formaldehyde). The first, methane conversion, step of these processes is the production of a synthesis gas ($CO+H_2$) by reforming of methane in the presence of steam over, for example, a nickel catalyst. Typical reformers are tubular furnaces heated with natural gas, the temperature being maintained at 900° C. and the pressure at about 225 atmospheres.

Pyrolytic or dehydrogenative conversion of methane or natural gas to $C_2+$ hydrocarbons has previously been proposed. The conversion requires high temperatures (greater than about 1000° C.) and is characterized by the formation of by-product hydrogen. The patent literature contains a number of proposals to catalyze pyrolytic reactions, allowing conversion at lower temperatures. See, for example, U.S. Pat. Nos. 1,656,813; 1,687,890; 1,851,726; 1,863,212; 1,922,918; 1,945,960; 1,958,648; 1,986,238 and 1,988,873. U.S. Pat. No. 2,436,595 discloses and claims a catalytic, dehydrogenative methane-conversion process which employs fluidized beds of heterogeneous catalysts comprising an oxide or other compound of the metals of group VI or VIII.

Including oxygen in a methane feed for conversion over metal oxide catalysts has been proposed. Margolis, L. Ya., Adv. Catal. 14, 429 (1963) and Andtushkevich, T. V., et al, Kinet. Katal. 6, 860 (1965) studied oxygen/methane cofeed over different metal oxides. They report the formation of methanol, formaldehyde, carbon monoxide and carbon dioxide from methane/oxygen feeds. Higher hydrocarbons are either not formed or are converted much faster than methane.

SUMMARY OF THE INVENTION

The copending, concurrently-filed U.S. applications cross-referenced above disclose and claim methods for the synthesis of higher hydrocarbon products from methane wherein a methane-containing gas is contacted with oxidative synthesizing agents. The presently claimed invention resides in the discovery that use of elevated pressures (i.e., pressures greater than atmospheric) in the methane-contact zone of processes employing one or more oxidative synthesizing agents promotes the formation of $C_3+$ hydrocarbon products. Methane contact zone pressures are preferably within the range of about 2 to 100 atmospheres, more preferably within the range of about 3 to 30 atmospheres.

BRIEF DESCRIPTION OF THE DRAWING

The FIGURE is a plot of the ratio, % yield of $C_3+$ hydrocarbon products/% yield of $C_2+$ hydrocarbon products, vs. run time for the instantaneous results obtained in Examples 1 and 2 and Comparative Example A.

DETAILED DESCRIPTION OF THE INVENTION

Oxidative synthesizing agents are compositions comprising at least one oxide of at least one metal, which composition, when contacted with methane at a temperature selected within the range of about 500° to 1000° C., produces C$_2$+ hydrocarbon products, co-product water, and a composition comprising a reduced metal oxide. The composition of the oxidative synthesizing agent thus contains at least one reducible oxide of at least one metal. The term "reducible" is used to identify those oxides of metals which are reduced by contact with methane at temperatures selected within the range of about 500° to 1000° C. The term "oxide(s) of metal(s)" includes: (1) one or more metal oxides (i.e., compounds described by the general formula M$_x$O$_y$ wherein M is a metal and the subscripts $_x$ and $_y$ designate the relative atomic proportions of metal and oxygen in the compound) and/or (2) one or more oxygen containing metal compounds, provided that such oxides and compounds have the capability of performing to produce higher hydrocarbon products as set forth herein.

Preferred oxidative synthesizing agents are disclosed in Ser. Nos. 522,925; 522,944; 522,942; 522,905; 522,877; 522,876; and 522,906; U.S. Pat. Nos. 4,443,649; 4,444,984; 4,443,648; 4,443,645; 4,443,647; 4,443,644; and 4,443,646. Thus, preferred oxidative synthesizing agents comprise reducible oxides of metals selected from the group consisting of Mn, Sn, In, Ge, Pb, Sb, and Bi, and mixtures thereof. Particularly preferred oxidative synthesizing agents comprise a reducible oxide of manganese and mixtures of a reducible oxide of manganese with other oxidative synthesizing agents. More preferred are oxidative synthesizing agents which comprise Mn$_3$O$_4$.

Reducible oxides are preferably provided as particles. They may be supported by, or diluted with, a conventional support material such as silica, alumina, titania, zirconia, and the like, and combinations thereof. A presently preferred support is silica.

Supported solids can be prepared by any suitable method. Conventional methods such as adsorption, impregnation, precipitation, coprecipitation, or dry-mixing can be used. A suitable method is to impregnate the support with solutions of compounds of the desired metal. Some examples of suitable compounds are the acetate, acetylacetonate, oxide, carbide, carbonate, hydroxide, formate, oxalate, nitrate, phosphate, sulfate, sulfide, tartrate, fluoride, chloride, bromide or iodide. After impregnation, the preparation is dried in an oven to remove solvent and the dried solid is prepared for use by calcining in air at temperatures selected within the range of about 300° to 1200° C. Particular calcination temperatures will vary depending upon the particular metal compound.

Metal loadings on supported solids vary be within the range of about 1 to 50 wt. % (calculated as the elemental metal(s) of the reducible oxide(s)).

The present process is distinguished from previously suggested methane conversion processes which rely primarily on interactions between methane and at least one of nickel and the noble metals, such as rhodium, palladium, silver, osmium, iridium, platinum and gold. An example of this type of process is disclosed in U.S. Pat. No. 4,205,194. The present process does not require that methane be contacted with one or more of nickel and such noble metals and compounds thereof.

Moreover, in a preferred embodiment, such contacting is carried out in the substantial absence of catalytically effective nickel and the noble metals and compounds thereof to minimize the deleterious catalytic effects of such metals and compounds thereof. For example, at the conditions, e.g., temperatures, useful for the contacting step of the present invention, these metals when contacted with methane tend to promote coke formation, and the metal oxides when contacted with methane tend to promote formation of combustion products (CO$_x$) rather than the desired hydrocarbons. The term "catalytically effective" is used herein to identify that quantity of one or more of nickel and the noble metals and compounds thereof which when present substantially changes the distribution of products obtained in the contacting step of this invention relative to such contacting in the absence of such metals and compounds thereof.

In addition to methane, the feedstock employed in the method of this invention may contain other hydrocarbon or nonhydrocarbon components, although the methane content should be within the range of about 40 to 100 vol. %, preferably from about 80 to 100 vol. %, more preferably from about 90 to 100 vol. %.

Operating temperatures for the contacting of methane-containing gas and the oxidative synthesizing agent are selected from the range of about 500° to 1000° C., the particular temperature selected depending upon the particular oxide(s) employed in the oxidative synthesizing agent.

For example, all oxidative synthesizing agents have the capability of synthesizing higher hydrocarbons from a methane source when the temperatures of the methane-contact are selected within the lower part of the recited range. Reducible oxides of certain metals, however, may require operating temperatures below the upper part of the recited range to minimum sublimation or volatilization of the metals (or compounds thereof) during methane contact. Examples are: (1) reducible oxides of indium (operating temperatures will preferably not exceed about 850° C.); (2) reducible oxides of germanium (operating temperatures will preferably not exceed about 800° C.); and (3) reducible oxides of bismuth (operating temperatures will preferably not exceed about 850° C.). Operating pressures for the methane contacting step of this invention are preferably within the range of about 2–100 atmospheres, more preferably about 3–30 atmospheres. Elevated pressures have been found to provide improved results, e.g., elevated pressures promote formation of C$_3$+ hydrocarbon products.

Contacting methane and an oxidative synthesizing agent to form higher hydrocarbons from methane also reduces the oxidative synthesizing agent and produces coproduct water. The exact nature of the reduced forms of oxidative synthesizing agents are unknown, and so are referred to herein as "reduced synthesizing agent" or as "a reduced metal oxide". Regeneration of a reducible oxide is readily accomplished by contacting reduced compositions with oxygen (e.g., an oxygen-containing gas such as air) at a temperature selected within the range of about 300° to 1200° C., the particular temperature selected depending on the particular metal(s) included in the oxidative synthesizing agent. The contact time should be sufficient to produce a reducible oxide from at least a portion of the reduced composition.

A single reactor apparatus containing a fixed bed of solids, for example, may be used with intermittent or pulsed flow of a first gas comprising methane and a second gas comprising oxygen (e.g., oxygen, oxygen diluted with an inert gas, or air, preferably air).

Preferably, the methane-contact step and the oxygen-contact step are performed in physically separate zones with particles recirculating between the two zones.

Thus, a suitable method for synthesizing hydrocarbons from a methane source comprises: (a) contacting a gas comprising methane and particles comprising an oxidative synthesizing agent to form higher hydrocarbon products, coproduct water, and particles comprising a reduced metal oxide; (b) removing particles comprising a reduced metal oxide from step (a) and contacting the reduced solids with an oxygen-containing gas to form particles comprising a reducible metal oxide; and (c) returning particles comprising a reducible metal oxide formed in step (b) to step (a). Steps (a), (b) and (c) are preferably repeated at least periodically, and more preferably the steps are continuous. Thus, in this more preferred embodiment, solids are continuously circulated between at least one methane-contact zone and at least one oxygen-contact zone. This more preferred embodiment is disclosed and claimed in copending, concurrently filed U.S. application Ser. No. (06/522,938).

Particles comprising a reducible metal oxide may be contacted with methane in fixed, moving, fluidized, ebullating, or entrained beds of solids. Preferably, methane is contacted with a fluidized bed of particles.

Similarly, particles comprising a reduced metal oxide may be contacted with oxygen in fixed, moving, fluidized, ebullating or entrained beds of solids. Preferably, oxygen is contacted with a fluidized bed of particles.

The invention is further illustrated by reference to the following examples. Experimental results reported below include conversions and selectivities calculated on a molar basis.

EXAMPLE 1

A supported oxide of manganese was prepared by impregnating the appropriate amount of manganese, as manganous acetate in a water solution, onto a Cab-O-Sil silica support. The impregnated solids were dried at 110° C. for 4 hours and then calcined in air at 700° C. for 16 hours. The composition of the calcined solids was 15 wt. % Mn/silica.

The finished solid was charged to a stainless steel tube (of $\frac{3}{8}$ inch inside diameter) surrounded by a tubular furnace. The interior walls of the stainless steel tube had been treated with potassium pyrophosphate to control coke formation catalyzed by the reactor wall. The contact zone temperature and pressure were raised to 700° C. and 100 psig, respectively, under flowing nitrogen. Nitrogen flow was stopped and methane was introduced into the contact zone at a GHSV (gas hourly space velocity) of 435 hrs.$^{-1}$. Reactor effluent was sampled at the reactor exit and analyzed on a gas chromatograph at a number of time intervals. In addition, all reactor effluent was collected in a sample bag for subsequent analysis of the cumulative reaction products. Results are reported in Table I below. The FIGURE shows a plot of the ratio, % yield of $C_3+$ hydrocarbon products/% yield of $C_2+$ hydrocarbon products, vs. run time for the instantaneous results obtained in this run.

TABLE 1

| Run Time (min.) | % Conversion | % Selectivity | | | | | |
|---|---|---|---|---|---|---|---|
| | | $C_2H_4$ | $C_2H_6$ | $C_3$ | $C_4$-$C_7$ | CO | $CO_2$ |
| Instantaneous Results | | | | | | | |
| 2 | 3.19 | 29.38 | 49.36 | 6.47 | 14.80 | 0 | 0 |
| 4 | 10.44 | 15.57 | 10.17 | 1.84 | 1.56 | 2.75 | 68.11 |
| 8 | 2.62 | 6.45 | 18.65 | 1.54 | 0.89 | 13.98 | 58.49 |

TABLE 1-continued

| Run Time (min.) | % Conversion | % Selectivity | | | | | |
|---|---|---|---|---|---|---|---|
| | | $C_2H_4$ | $C_2H_6$ | $C_3$ | $C_4$-$C_7$ | CO | $CO_2$ |
| 16 | 1.23 | 0 | 78.80 | 4.73 | 1.55 | 14.93 | 0 |
| Cumulative Results | | | | | | | |
| 30 | 2.47 | | 3.78 | 35.22 | 3.43 | 1.86 | 34.14 | 21.57 |

EXAMPLE 2

The procedure of Example 1 was repeated except that the methane feed rate was increased to provide a GHSV of 2392 hrs.$^{-1}$. The FIGURE shows a plot of the ratio, % yield of $C_3+$ hydrocarbon products/% yield of $C_2+$ hydrocarbon products vs. run time for the instantaneous results obtained in this run.

COMPARATIVE EXAMPLE A

The procedure of Example 1 was repeated except that the pressure in the contact zone during the methane run was 0 psig. The FIGURE shows a plot of the ratio, % yield of $C_3+$ hydrocarbon products/% yield of $C_2+$ hydrocarbon products, vs. run time for the results obtained in this run.

EXAMPLES 3-4

Following the same preparative procedure described in Example 1, a composition containing 5 wt. % $Mn/SiO_2$ was prepared and contacted with methane (as described in Example 1) under the operating conditions shown in Table II below. Table II also shows instantaneous results (i.e., % methane conversion and % selectivity to $C_3+$ hydrocarbon products) obtained at 2.0 and 1.0 minutes, respectively, in Examples 3 and 4.

EXAMPLE 5

A supported oxide of indium was prepared by impregnating the appropriate amount of indium, as indium nitrate in a water solution, onto a silica support. The impregnated solids were dried at 110° C. for 2 hours. The dried solid was then heated to 700° C. at 2°/minute and held at 700° C. for 10 hours in air to give a finished solid containing 5 wt. % In. This solid was contacted with methane as described in Example 1 under the operating conditions shown in Table II below. Table II also show instantaneous results obtained at 2.0 minutes after the start of the methane contact.

COMPARATIVE EXAMPLE B

Methane was contacted, at atmospheric pressure, with a bed of 5 wt. % $Mn/SiO_2$ (prepared as described in Example 1) in a quartz tube reactor (12 mm. inside diameter) packed with 10 ml. of the solid. The temperature in the contact zone was maintained at 700° C. and the GHSV was 600 hrs.$^{-1}$. Instantaneous results obtained at a run time of 2 minutes are shown in Table II below.

COMPARATIVE EXAMPLE C

Methane was contacted, at atmospheric pressure, with a bed of 5 wt. % $In/SiO_2$ (prepared as described in Example 5) in a quartz tube reactor (0.5 inch inside diameter) packed with 2.7 grams of the solid. The temperature in the contact zone was maintained at 700° C. and the GHSV was 860 hrs.$^{-1}$. Instantaneous results obtained at run time of 1.0 and 3.0 minutes are shown in Table II below.

TABLE II

| Example | Solid | Pressure (psig) | Temp (°C.) | GHSV | Run Time (min.) | % Conversion | % Selectivity to C3+ hydrocarbon |
|---|---|---|---|---|---|---|---|
| 3 | 5% Mn/SiO2 | 100 | 700 | 600 | 2.0 | 10.4 | 22.0 |
| B | 5% Mn/SiO2 | 0 | 700 | 600 | 2.0 | 1.95 | 0.9 |
| 4 | 5% Mn/SiO2 | 100 | 800 | 3120 | 1.0 | 14.1 | 32.0 |
| 5 | 5% In/SiO2 | 100 | 700 | 600 | 2.0 | 6.8 | 28.1 |
| C | 5% In/SiO2 | 0 | 700 | 860 | 1.0 | 0.73 | 0.3 |
| | | | | | 3.0 | 0.31 | 0.7 |

What is claimed is:

1. In an improved method for converting methane to higher hydrocarbon products which comprises contacting a gas comprising methane at synthesizing conditions with at least one reducible oxide of at least one metal which oxides when contacted with methane at synthesizing conditions are reduced and produce higher hydrocarbon products and water, the improvement which comprises conducting said contacting at a pressure greater than atmospheric pressure.

2. The method of claim 1 wherein the pressure is within the range of about 2 to 100 atmospheres.

3. The method of claim 1 wherein the pressure is within the range of about 3 to 30 atmospheres.

4. The method of claim 1 wherein said contacting is carried out in the substantial absence of catalytically effective Ni, Rh, Pd, Ag, Os, Ir, Pt, Au and compounds thereof.

5. A method for converting methane to higher hydrocarbon products by contacting methane with an oxidative synthesizing agent comprising at least one reducible oxide of at least one metal selected from the group consisting of Mn, Sn, In, Ge, Pb, Sb, and Bi; which method comprises contacting a gas comprising methane and said oxidative synthesizing agent at a pressure greater than atmospheric pressure.

6. The method of claim 5 wherein the pressure is within the range of about 2 to 100 atmospheres.

7. The method of claim 5 wherein the pressure is within the range of about 3 to 30 atmospheres.

8. The method of claim 5 wherein the temperature of said contact is selected within the range of about 500° to 1000° C.

9. The method of claim 7 wherein the temperature of said contact is selected within the range of about 500° to 1000° C.

10. The method of claim 5 wherein the gas comprising methane contains about 40 to 100 vol. % methane.

11. The method of claim 5 wherein the gas comprising methane contains about 80 to 100 vol. % methane.

12. The method of claim 5 wherein the gas contains about 90 to 100 vol. % methane.

13. The method of claim 5 wherein the gas comprising methane is natural gas.

14. The method of claim 5 wherein the gas comprising methane is processed natural gas.

15. The method of claim 5 wherein a gas consisting essentially of methane is contacted with the said agent.

16. The method of claim 5 wherein the metal selected is Mn.

17. The method of claim 16 wherein said contacting is carried out in the substantial absence of catalytically effective Ni, Rh, Pd, Ag, Os, Ir, Pt, Au and compounds thereof.

18. The method of claim 16 wherein the reducible oxide of Mn is $Mn_3O_4$.

19. The method of claim 5 wherein the metal selected is Sn.

20. The method of claim 19 wherein the reducible oxide of of Sn is $SnO_2$.

21. The method of claim 5 wherein the metal selected is In.

22. The method of claim 21 wherein said contacting is carried out in the substantial absence of catalytically effective Ni, Rh, Pd, Ag, Os, Ir, Pt, Au and compounds thereof.

23. The method of claim 21 wherein the reducible oxide of In is $In_2O_3$.

24. The method of claim 5 wherein the metal selected is Ge.

25. The method of claim 24 wherein the reducible oxide of Ge is $GeO_2$.

26. The method of claim 5 wherein the metal selected is Pb.

27. The method of claim 26 wherein the reducible oxide of Pb is PbO.

28. The method of claim 5 wherein the metal selected is Sb.

29. The method of claim 26 wherein the reducible oxide of Sb is $Sb_2O_3$.

30. The method of claim 5 wherein the metal selected is Bi.

31. The method of claim 30 wherein the reducible oxide of Bi is $Bi_2O_3$.

32. The method of claim 16 wherein the temperature of said contacting is within the range of about 500° to 1000° C.

33. The method of claim 19 wherein the temperature of said contacting is within the range of about 500° to 1000° C.

34. The method of claim 26 wherein the temperature of said contacting is within the range of about 500° to 1000° C.

35. The method of claim 26 wherein the temperature of said contacting is within the range of about 500° to 1000° C.

36. The method of claim 21 wherein the temperature of said contacting is within the range of about 500° to 850° C.

37. The method of claim 30 wherein the temperature of said contacting is within the range of about 500° to 850° C.

38. The method of claim 22 wherein the temperature of said contacting is within the range of about 500° to 800° C.

* * * * *